(12) United States Patent
Joshi

(10) Patent No.: US 9,225,194 B2
(45) Date of Patent: Dec. 29, 2015

(54) IMPLANTABLE MEDICAL DEVICE CHARGING APPARATUS HAVING BOTH PARALLEL AND SERIES RESONATORS

(71) Applicant: CYBERONICS, INC., Houston, TX (US)

(72) Inventor: Himanshu Joshi, Houston, TX (US)

(73) Assignee: CYBERONICS, INC., Houston, TX (US)

( * ) Notice: Subject to any disclaimer, the term of this patent is extended or adjusted under 35 U.S.C. 154(b) by 300 days.

(21) Appl. No.: 13/869,484

(22) Filed: Apr. 24, 2013

(65) Prior Publication Data

US 2014/0320074 A1 Oct. 30, 2014

(51) Int. Cl.
*H02J 7/00* (2006.01)
*A61N 1/00* (2006.01)
*H02J 7/02* (2006.01)
*H01F 38/14* (2006.01)
*A61N 1/378* (2006.01)
*A61N 1/372* (2006.01)

(52) U.S. Cl.
CPC ............ *H02J 7/025* (2013.01); *A61N 1/3787* (2013.01); *H01F 38/14* (2013.01); *A61N 1/37223* (2013.01)

(58) Field of Classification Search
CPC ........ H02J 7/025; H01F 38/14; A61N 1/3787
USPC ...................... 320/108; 607/33, 61
See application file for complete search history.

(56) References Cited

U.S. PATENT DOCUMENTS

| | | | |
|---|---|---|---|
| 4,209,783 A * | 6/1980 | Ohyama et al. | ............ 340/10.42 |
| 4,513,260 A * | 4/1985 | Ragan | ............ 333/165 |
| 4,561,443 A | 12/1985 | Hogrefe et al. | |
| 4,665,896 A | 5/1987 | La Forge et al. | |
| 5,154,172 A | 10/1992 | Terry, Jr. et al. | |
| 5,222,494 A | 6/1993 | Baker, Jr. | |
| 6,516,227 B1 | 2/2003 | Meadows et al. | |
| 6,972,543 B1 | 12/2005 | Wells | |
| 7,177,691 B2 | 2/2007 | Meadows et al. | |
| 7,729,760 B2 | 6/2010 | Patel et al. | |
| 7,751,891 B2 | 7/2010 | Armstrong et al. | |
| 7,769,466 B2 | 8/2010 | Denker et al. | |
| 9,041,484 B2 * | 5/2015 | Burgener et al. | ............ 333/101 |
| 2005/0075697 A1 | 4/2005 | Olson et al. | |

(Continued)

FOREIGN PATENT DOCUMENTS

GB 2297037 A 7/1996

OTHER PUBLICATIONS

Yungtaek Jang et al., "A Contactless Electrical Energy Transmission System for Portable-Telephone Battery Chargers," IEEE Transactions on Industrial Electronics, vol. 50, No. 3, Jun. 2003, pp. 520-527.

(Continued)

*Primary Examiner* — M'baye Diao
(74) *Attorney, Agent, or Firm* — Cyberonics, Inc.

(57) ABSTRACT

An implantable medical device charging apparatus includes a charging circuit. The charging circuit includes a series resonator responsive to a signal applied to the charging circuit. During operation, the series resonator inductively couples to a secondary coil within an implantable medical device to transfer energy to the secondary coil. The charging circuit also includes a parallel resonator coupled to the series resonator. The parallel resonator filters a first component of the signal from propagating to the series resonator.

20 Claims, 3 Drawing Sheets

(56) References Cited

U.S. PATENT DOCUMENTS

| | | | |
|---|---|---|---|
| 2006/0247737 A1 | 11/2006 | Olson et al. | |
| 2007/0030096 A1* | 2/2007 | Nishihara et al. | 333/133 |
| 2009/0121806 A1* | 5/2009 | Sasaki et al. | 333/174 |
| 2009/0210035 A1 | 8/2009 | Gelbart | |
| 2009/0268647 A1* | 10/2009 | Uejima | 370/297 |
| 2010/0137948 A1 | 6/2010 | Aghassian et al. | |
| 2010/0171565 A1* | 7/2010 | Okada | 333/132 |
| 2010/0174348 A1* | 7/2010 | Bulkes et al. | 607/116 |
| 2010/0245186 A1* | 9/2010 | Kojima | 343/702 |
| 2011/0046699 A1 | 2/2011 | Mazanec | |
| 2012/0086281 A1* | 4/2012 | Kanno | 307/82 |
| 2012/0262108 A1 | 10/2012 | Olson et al. | |
| 2012/0277831 A1 | 11/2012 | Joshi | |
| 2014/0285016 A1* | 9/2014 | Tetu et al. | 307/31 |

OTHER PUBLICATIONS

Sung-Noon Cho et al., "A Wireless Powered Fully Integrated SU-8-Based Implantable LC Transponder," Technical Paper, Microsyst Technol, Springer-Verlag 2010, Received Jul. 17, 2009, Accepted Feb. 16, 2010, Published Online, Mar. 9, 2010, 7 pages.

Gurhan Alper Kendir et al., "An Optimal Design Methodology for Inductive Power Link with Class-E Amplifier," IEEE Transactions on Circuits and Systems—I: Regular Papers, vol. 52, No. 5, May 2005, pp. 857-866.

International Application No. PCT/US2014/031664; PCT Search Report and Written Opinion dated Jul. 2, 2014, 7 pages.

\* cited by examiner

IMPLANTABLE MEDICAL DEVICE CHARGING APPARATUS HAVING BOTH PARALLEL AND SERIES RESONATORS

FIELD OF THE DISCLOSURE

The present disclosure is generally related to implantable medical devices.

BACKGROUND

Advances in technology have led to the development of miniature medical devices that can be implanted within a living organism, such as a human, to provide treatment or monitoring. Powering such implantable medical devices can be a concern. For example, some implantable medical devices use an onboard battery as a power source. However, since batteries store a finite amount of energy, an onboard battery may only be a temporary power source. Replacing batteries for implantable medical devices may be expensive and inconvenient. For example, depending on the specific nature of the implantable medical device, surgery may be needed to replace the device or to replace the battery.

Due to these and other concerns, some implantable medical devices use rechargeable batteries. However, recharging batteries that are located inside a device that is implanted in a patient presents other concerns. For example, when long charging times are required, patient compliance can be a problem. As another example, recharging batteries may cause an increase in radiation between the implantable medical device and an external system, such as a portable hand-held system used for recharging the batteries and used for communicating data to and from the implantable medical device. Increases in radiation may cause noise, which may cause errors when communicating data between the implantable medical device and external system.

SUMMARY

A battery onboard an implantable medical device can be recharged using an inductively-coupled recharging system. For example, a device (e.g., an implantable medical device charging apparatus) that is external to a patient may include a charging circuit coupled to a series resonator that includes a primary coil. The implantable medical device may include a recharging circuit coupled to a secondary coil. The primary and secondary coils may be inductively coupled to enable transfer of energy from the primary coil to the secondary coil. The charging circuit may provide energy received by the secondary coil from the primary coil to a battery. Thus, the inductively-coupled recharging system enables the battery to be wirelessly recharged from a source external to the patient via the inductive coupling of the primary and secondary coils.

The implantable medical device may be programmable by an external signaling device. The external signaling device may be distinct (e.g., a separate device) or may be a component of, or integrated with, the device that is external to the patient. For example, the external signaling device (e.g., a first antenna or a first communication coil) may be used to communicate data to and from the implantable medical device via an internal signaling device (e.g., a second antenna or a second communication coil) of the implantable medical device. Data may be transferred between the external signaling device and the internal signaling device at a first frequency within a first frequency band. The series resonator used to recharge the implantable medical device may resonate at a second frequency within a second frequency band (e.g., a frequency band at a lower frequency range than the first frequency band) to provide energy to the secondary coil.

When components of a charging signal provided to the charging circuit are within, or approximate to, the first frequency band, radiation at the primary coil may generate noise, which may interfere with data communication between the external signaling device and the internal signaling device. In addition, the primary coil may radiate at a frequency (e.g., the first frequency) used to communicate data, which may cause errors in data communication. Thus, it may be difficult for the device external to the patient to communicate data to the implantable medical device while charging the implantable medical device.

The circuitry used to generate the charging signal may use switching circuitry. Switching noise generated by the switching circuitry may couple on to wire leads and interfere with a stimulation signal or a sensing signal if the implantable medical device uses wire leads for electrical stimulation and/or sensing. Thus, stimulation dosing may be less precise and sensing may be less reliable.

To address such concerns, a parallel resonator may be implemented within the charging circuit to attenuate power that corresponds to high frequency components of the charging signal that would otherwise flow through the primary coil of the series resonator. For example, when the charging signal has a frequency component within the first frequency band (e.g., a high frequency harmonic component), the parallel resonator may resonate and behave in a manner similar to an open circuit. As a result, the high frequency harmonic component and/or noise may be substantially inhibited from propagating to the series resonator (and to the primary coil), thus attenuating an amount of noise and radiation at the primary coil during energy transfer. Communication between the external and internal signaling devices is improved by the reduced noise at the primary coil. Thus, in a particular embodiment, the parallel resonator may substantially inhibit (e.g., filter) high frequency components of the charging signal from flowing through the primary coil of the series resonator to reduce noise and radiation at the primary coil (and to improve communication, stimulation dosing, sensing, or a combination thereof).

In a particular embodiment, the parallel resonator may include a torodial inductor that is coupled to a board of the charging circuit to reduce or eliminate radiation at the parallel resonator. The parallel resonator, designed to resonate at a frequency higher than the second frequency (e.g., the recharge frequency), may have an effective inductance at the second frequency. The effective inductance of the parallel resonator at the charging signal frequency may be added to the inductance of the series resonator when the charging signal has a frequency component within the second frequency band. As a result, the series resonator may use a smaller inductor (e.g., a smaller primary coil), thus improving the efficiency of the energy transfer substantially maintaining the total inductance of the charging circuit.

In a particular embodiment, an implantable medical device charging apparatus includes a charging circuit. The charging circuit includes a series resonator responsive to a signal applied to the charging circuit. During operation, the series resonator inductively couples to a secondary coil within an implantable medical device to transfer energy to the secondary coil. The signal includes a first component having a first frequency within a first frequency band and a second component having a second frequency within a second frequency band. The charging circuit also includes a parallel resonator coupled to the series resonator. The parallel resonator filters the first component of the signal from propagating to the series resonator.

In a particular embodiment, a method of charging an implantable medical device includes generating a signal at an external device. The signal has a first component having a first frequency within a first frequency band and has a second component having a second frequency within a second frequency band. The method also includes applying the signal to a charging circuit. The charging circuit includes a series resonator and a parallel resonator. The parallel resonator resonates in response to the first component of the signal and provides the second component of the signal to the series resonator. The second component of the signal causes a primary coil of the series resonator to inductively couple to a secondary coil of an implantable medical device.

In a particular embodiment, a circuit for charging an implantable medical device includes a signal generator and a parallel resonator coupled to the signal generator. The signal generator generates a signal having a first component having a first frequency within a first frequency band and a second component having a second frequency within a second frequency band. The parallel resonator includes a parallel inductor and a parallel capacitor. The circuit also includes a series resonator coupled to the parallel resonator to inductively transfer energy to the secondary coil within the implantable medical device. The series resonator includes a capacitor and a primary coil. The parallel resonator inhibits the first component from propagating to the series resonator and provides the second component of the signal to the series resonator.

The features, functions, and advantages that have been described can be achieved independently in various embodiments or may be combined in yet other embodiments, further details of which are disclosed with reference to the following description and drawings.

DETAILED DESCRIPTION

Figure 1:
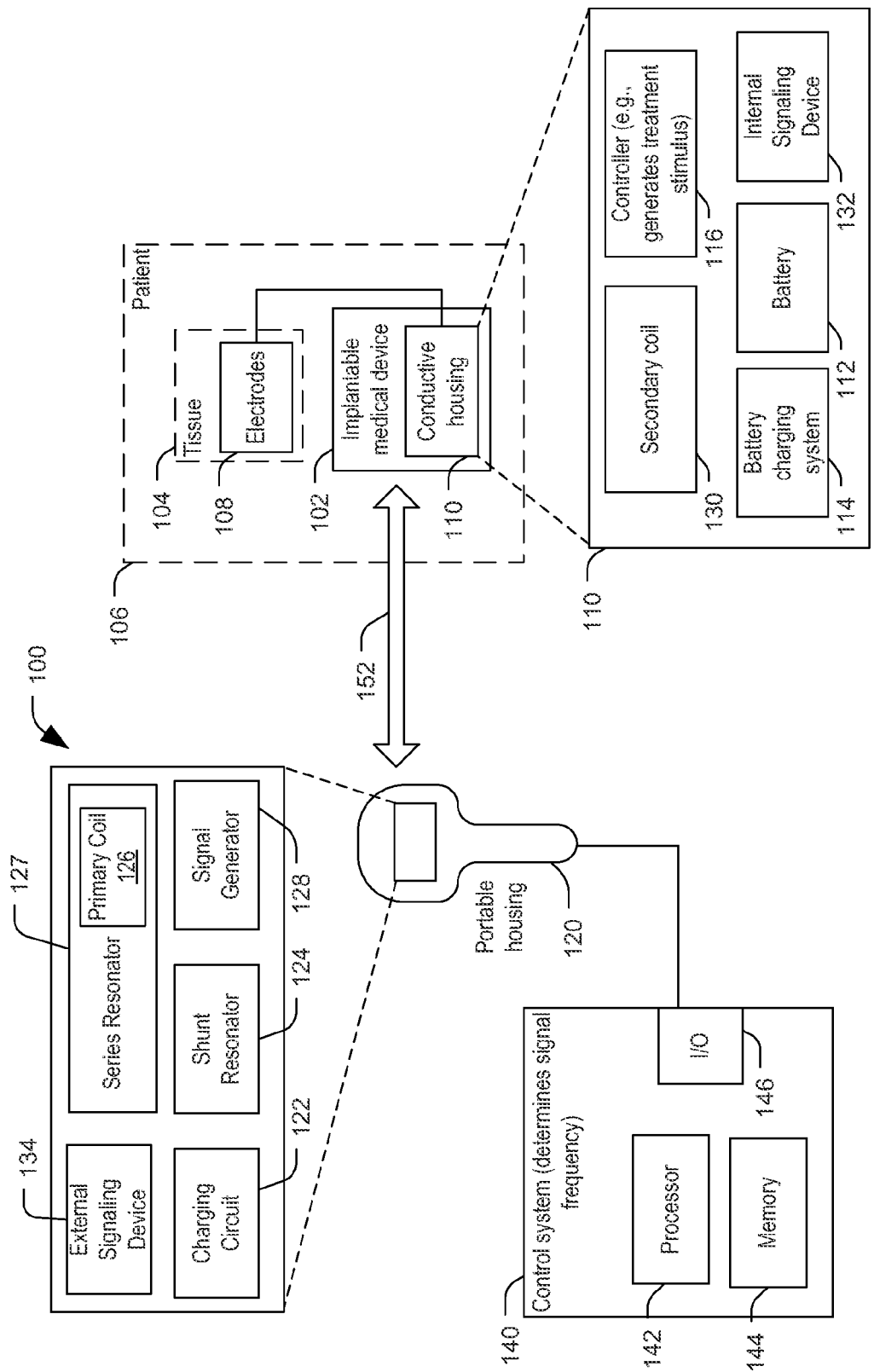
FIG. 1 is a block diagram of a particular embodiment of an implantable medical device and a charging system.

FIG. 1 is a block diagram of a particular embodiment of an implantable medical device 102 and an external device 100. In a particular embodiment, the external device 100 is an implantable medical device charging apparatus configured to charge the implantable medical device 102. In another particular embodiment, the external device 100 is a device that is configured to communicate data with the implantable medical device 102 and that includes a component (e.g., an implantable medical device charging apparatus) to charge the implantable medical device 102.

The implantable medical device 102 may be adapted to be surgically implanted in a patient 106 to provide therapy, to monitor one or more conditions, for another purpose, or any combination thereof. In a particular embodiment, the implantable medical device 102 may be coupled to one or more electrodes 108 and may be adapted to deliver electrical stimulus to tissue 104 of the patient 106 via the electrodes 108. In a particular embodiment, the implantable medical device 102 is an implantable nerve stimulation device. Examples of the implantable nerve stimulation device may include an implantable vagus nerve stimulation device, an implantable spinal cord stimulation device, etc. The electrodes 108 may be coupled to the implantable medical device 102 and may be positioned proximate to or coupled to a nerve, such as a cranial nerve (e.g., the trigeminal nerve, the hypoglossal nerve, the vagus nerve, a branch of the vagus nerve, glossopharyngeal nerve, or a combination thereof). The implantable medical device 102 may include a controller 116 that is configured to control generation of treatment stimulus provided to the electrodes 108 to provide an electrical stimulus to the tissue 104. In another particular embodiment, the implantable medical device 102 is an implantable drug pump. In another particular embodiment, the implantable medical device 102 is an implantable sensor. Examples of an implantable sensor may include an electrocardiogram (ECG) sensor, an electroencephalogram (EEG) sensor, etc. Note that the term "patient" is used broadly to include any organism and is not intended to imply that the patient 106 is human; although the patient 106 is a human patient in one embodiment.

In a particular embodiment, the implantable medical device 102 may include a conductive housing 110. One or more of a battery 112, a battery charging system 114, a secondary coil 130, and other components of the implantable medical device 102 may be enclosed in the conductive housing 110. The implantable medical device 102 may include a power supply, such as the battery 112, that stores power to operate the implantable medical device 102. The battery charging system 114 may be configured to receive power from the external device 100 to recharge the battery 112. For example, the external device 100 may include a series resonator 127. The series resonator 127 may include a primary coil 126 that is configured to inductively couple 152 to the secondary coil 130 within the implantable medical device 102. The series resonator 127 may be responsive to a charging signal generated by a signal generator 128 and applied to a charging circuit 122 of the external device 100. The signal generator 128 may include switching circuitry that may result in switching noise on the charging signal. The charging circuit 122 may include or be coupled to the primary coil 126. The primary coil 126 may transfer energy to the secondary coil 130. For example, in a particular embodiment, the primary coil 126 may function as a primary winding of a transformer and the secondary coil 130 may function as a secondary winding of a transformer. The battery charging system 114 may be coupled to the secondary coil 130 and may be configured to receive a current from the secondary coil 130 and to apply a charging voltage to the battery 112 responsive to the current.

The external device 100 may also include an external signaling device 134. Alternatively or in addition, the external signaling device 134 may be a component of another external device (not shown). The implantable medical device 102 may include an internal signaling device 132. The external device 100 may communicate data with the implantable medical device 102 over a first frequency band using the external and internal signaling devices 134, 132. The first frequency band may range from about 60 kilohertz (kHz) to about 100 kHz, and data may be communicated over a particular frequency (e.g., about 75 kHz) within the first frequency band. In a particular embodiment, the external signaling device 134 may include a first antenna and the internal signaling device 132 may include a second antenna. In some embodiments, the first frequency band may correspond to switching noise and may range from about 50 megahertz (MHz) to about 100 MHz, 100 MHz to 500 MHz, or any other high frequency associated with switching noise. In a particular embodiment, the switching noise may have a frequency of approximately 85 MHz The external device 100 may be configured to receive information from the implantable medical device 102 using the external and internal signaling devices 134, 132. For example, the external device 100 may receive information that is indicative of an electrical property associated with the implantable medical device 102 or an electrical property associated with a component of the implantable medical device 102, such as the battery 112, the battery charging system 114, another component of the implantable medical device 102, or any combination thereof. For example, the implantable medical device 102 may include a measurement system (not shown). The measurement system may measure the electrical property of the implantable medical device 102 or of the component of the implantable medical device 102, and the implantable medical device 102 may provide the information indicative of the electrical property to the external device 100 via wireless communication between the first and second signaling devices 134, 132. The electrical property measured by the measurement system may include a charge level of the battery 112, a voltage or current applied to the battery 112 by the battery charging system 114, another indication of an amount of power applied by the battery charging system 114 to the battery 112, another electrical property of a component of the implantable medical device 102, or any combination thereof.

The external device 100 may also include a parallel resonator 124 coupled to the series resonator 127. In a particular embodiment, the parallel resonator 124 and the series resonator 127 may be included in the charging circuit 122. The parallel resonator 124 may resonate at about the same frequency used to communicate data within the first frequency band. For example, the parallel resonator 124 may resonate in response to a 75 kHz signal. In another particular embodiment, the parallel resonator 124 may resonate at about the same frequency as the switching noise caused by the switching circuitry of the signal generator 128 within the first frequency band. For example, the parallel resonator 124 may resonate in response to an 85 MHz signal. In another particular embodiment, two or more parallel resonators may be used to resonate in response to two or more high frequency signals, respectively (e.g., 75 kHz and 85 MHz). The series resonator 127 may resonate at a lower frequency in a second frequency band. For example, the second frequency band may range from about 9 kHz to about 11 kHz, and the series resonator 127 may resonate in response to a 10 kHz signal.

The parallel resonator 124 is configured to reduce noise and radiation generated at the primary coil 126 of the series resonator 127 when the charging signal applied to the charging circuit 122 has a frequency component within the first frequency band (e.g., a high frequency component). For example, the signal generator 128 within, or coupled to, the charging circuit 122 may generate a charging signal having frequency components within the first frequency band (e.g., high frequency components) and frequency components within the second frequency band (e.g., low frequency components). As described with respect to FIG. 2, the parallel resonator 124 is configured to substantially inhibit (e.g., filter, block, or prevent) the high frequency components of the charging signal from propagating to the series resonator 127 and to provide the low frequency components of the charging signal to the series resonator 127. For example, the parallel resonator 124 may operate as an open circuit to filter the harmonics corresponding to the high frequency components of the charging signal from propagating to the series resonator 127. Filtering harmonics that correspond to the high frequency components of the charging signal may include reducing an amount of current, and thus an amount of power, in the portions of the charging signal that correspond to a frequency approximately within a 60 kHz to 100 kHz range, a 50 MHz to 100 MHz range, or a combination thereof.

Filtering the harmonics of the charging signal that correspond to the high frequency components within the first frequency band may also facilitate simultaneously charging the implantable medical device 102 using the charging signal and communicating data to a receiver within the implantable medical device 102 using a communication signal within the first frequency band. For example, filtering the high frequency components of the charging signal may reduce a likelihood of signal interference with the communication signal, which may cause errors during data communication.

The parallel resonator 124 is further configured to contribute to the inductance of the series resonator 127 for the low frequency components of the charging signal generated by the signal generator 128. For example, in a low frequency range, the parallel resonator 124 may have an effective inductance and may provide the low frequency components of the charging signal to the series resonator 127. The effective inductance of the parallel resonator 124 may be added to the inductance of the series resonator 127 (e.g., the inductance of the primary coil 126) increasing an effective coil size of the primary coil 126, which may enable use of a smaller primary coil 126 without affecting the total inductance. The parallel resonator 124 may include a torodial inductor coupled to a board of the charging circuit 122 to minimize or reduce radiation at the parallel resonator 124.

The external device 100 may include a control system 140. The control system 140 may control application of charging signals generated by the signal generator 128. The control system 140 may include one or more processors, such as a processor 142, and memory accessible to the processor 142, such as a memory 144. The memory 144 may include tangible, non-transitory, computer-readable media (e.g., one or more computer memory devices). The processor 142 may be implemented using a single-chip processor or using multiple processors. The memory 144 may include various memory devices, such as registers, cache, volatile memory, and non-volatile memory. For example, the memory 144 can include cache that is accessible by the processor 142 to rapidly retrieve and store data. The memory 144 can include any data storage device that can store data which can thereafter be read by the control system 140 or by another computing system. Examples of computer-readable media that the memory 144 may use include, but are not limited to: magnetic media such as hard disks, floppy disks, and magnetic tape; optical media such as CD-ROM disks; magneto-optical media; and specially configured hardware devices such as application-specific integrated circuits (ASICs), programmable logic devices (PLDs), and ROM and RAM devices.

The memory 144 may store instructions that are executable by the processor 142 to implement various functions of the control system 140. To illustrate, the instructions may be executable by the processor 142 to control charging signals generated by the signal generator 128, to process information received from the implantable medical device 102, and so forth. For example, the instructions may be executable by the processor 142 to control the characteristics (e.g., frequency, amplitude, duty cycle, polarity, pulse width, pulse period, signal duration, etc.) of the charging signal generated by the signal generator 128 within, or coupled to, the charging circuit 122.

Additionally or in the alternative, the control system 140 may include dedicated hardware implementations, such as application specific integrated circuits, programmable logic arrays and other hardware devices, to implement one or more functions of the control system 140. Accordingly, the present disclosure encompasses software, firmware, and hardware implementations.

The control system 140 may also include an input/output (I/O) interface 146. The I/O interface 146 may enable the control system 140 to send and receive information and signals to other components of the external device 100. For example, the charging circuit 122 and the primary coil 126 (as well as one or more other components) may be housed within a portable housing 120, such as a handheld wand or other device. The control system 140 may send control information and signals to the portable housing 120 via the I/O interface 146 and may receive information from the portable housing 120 via the I/O interface 146.

During operation, the signal generator 128 may generate a charging signal having high frequency components within the first frequency band and low frequency components within the second frequency band. The parallel resonator 124 may attenuate power corresponding to the high frequency components and provide the low frequency components of the charging signal to the series resonator 127. For example, the parallel resonator 124 may reduce or eliminate current corresponding to high frequency components of the charging signal from propagating to the series resonator 127. As described with respect to FIG. 2, the parallel resonator 124 may resonate in response to the high frequency components of the charging signal, causing the parallel resonator 124 to function as an open circuit, thus reducing or eliminating current corresponding to the high frequency components of the charging signal from propagating to the series resonator 127. The portions of the charging signal that have low frequency components may propagate through an inductor (not shown) of the parallel resonator 124 and may be provided to the series resonator 127, causing the series resonator 127 to resonate. The primary coil 127 inductively couples 152 to the secondary coil 130 of the implantable medical device 102 using the portions of the charging signal with the low frequency components to charge the implantable medical device 102. Noise in a high frequency range (e.g., a frequency range used for data communication or higher) may be reduced during inductive coupling 152 by inhibiting (e.g., filtering) high frequency components of the charging signal.

The external device 100 may charge the implantable medical device 102 using low frequency components of the charging signal within the second frequency band while simultaneously communicating data to a receiver within the implantable medical device 102 using a high frequency communication signal (e.g., a 75 kHz signal) within the first frequency band. The parallel resonator 127 may substantially inhibit (e.g., filter, block, or prevent) high frequency components of the charging signal from propagating to the series resonator 127 and may provide low frequency components of the charging signal to the series resonator 127 to charge the battery 112 of the implantable medical device 102. Meanwhile, the external device 100 may communicate with the implantable medical device 102 using a frequency that corresponds to the high frequency components that are filtered by the parallel resonator 127. Charging the implantable medical device 102 using the low frequency components of the charging signal while the parallel resonator 124 filters the high frequency components of the charging signal may facilitate simultaneous charging of the implantable medical device 102 and data communication with the implantable medical device 102. For example, filtering the high frequency components of the charging signal may reduce a likelihood of signal interference, which may cause errors during data communication.

In some embodiments, the parallel resonator 124 may be provided to substantially inhibit (e.g., filter, block, or prevent) high frequency components of the charging signal (e.g., 85 MHz) caused by switching noise from propagating to the series resonator 127 and may provide low frequency components of the charging signal to the series resonator 127 to charge the battery 112 of the implantable medical device 102.

Figure 2:
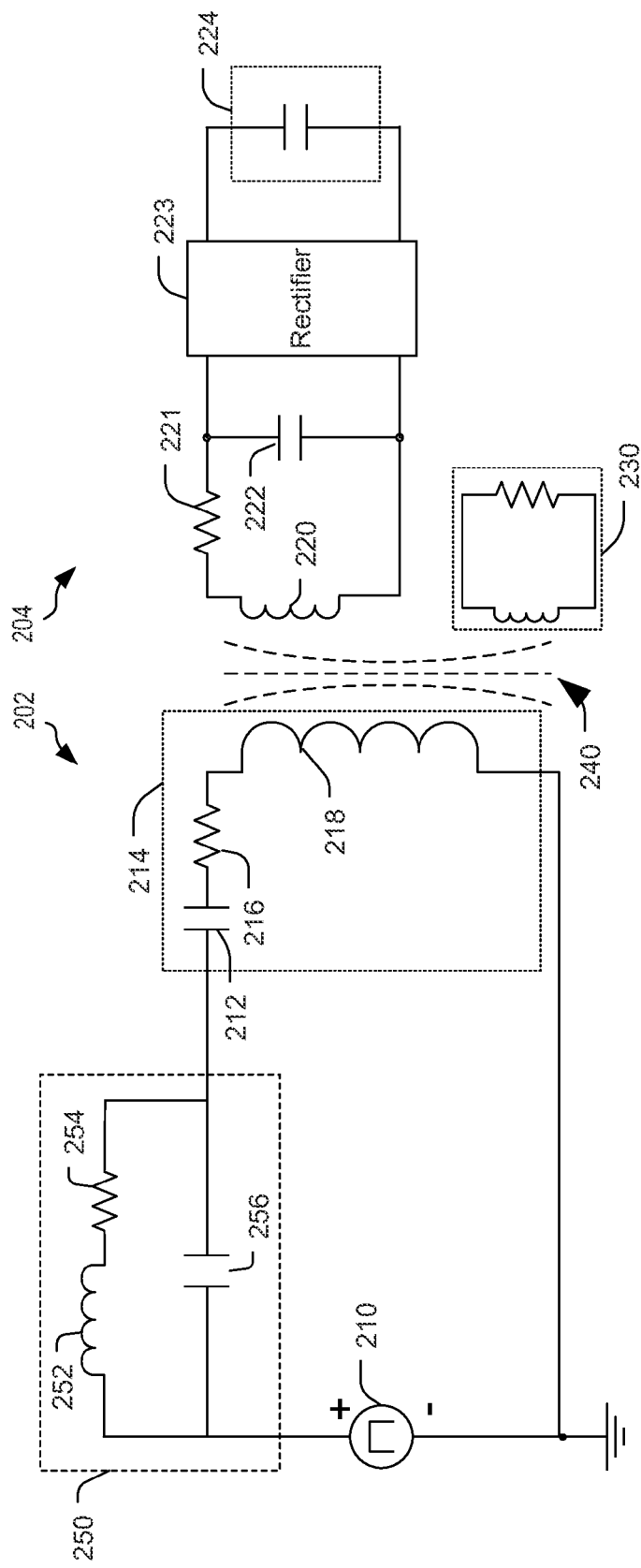
FIG. 2 is a simplified circuit diagram of a particular embodiment of an implantable medical device and a charging system.

FIG. 2 is a simplified circuit diagram of a particular embodiment of an implantable medical device and a charging circuit. In particular, the simplified circuit diagram illustrates an external charging circuit 202 that is inductively coupled 240 to an internal system, such as an implantable medical device 204. Power may be transferred from the external charging circuit 202 to the implantable medical device 204 to recharge a power source of the implantable medical device 204 via inductive coupling 240. In a particular embodiment, the external charging circuit 202 may include, be included within, or correspond to the external device 100 of FIG. 1. For example, in a particular embodiment, the external charging circuit 202 may include the charging circuit 122 of FIG. 1 and may operate in a substantially similar manner. Further, the implantable medical device 204 may correspond to the implantable medical device 102 of FIG. 1 and may operate in a substantially similar manner.

In a particular embodiment, the implantable medical device 204 includes a secondary coil 220, a secondary resistor 221 (e.g., may correspond to resistive losses of the secondary coil 220), and a secondary capacitor 222. The secondary coil 220, the secondary resistor 221, and the secondary capacitor 222 may be included in a resistive (R), inductive (L), and capacitive (C) circuit (also referred to as an "RLC circuit"). The RLC circuit comprising the secondary coil 220, the secondary resistor 221, and the secondary capacitor 222 may resonate in response to a charging signal within the second frequency band (e.g., from about 9 kHz to 11 kHz).

The implantable medical device 204 also includes a rectifier 223 and a rechargeable power supply 224 (such as a battery, a capacitor, or another energy storage device). For example, the rechargeable power supply 222 may include or be included within the battery 112 of the FIG. 1. Current generated at the RLC circuit of the implantable medical device 204 may be applied to the rectifier 223 and then to the rechargeable power supply 224 as a rectified voltage to charge the rechargeable power supply 224. The implantable medical device 204 may include a conductive housing 230. The conductive housing 230 is illustrated separately from the implantable medical device 204 to illustrate the inductive coupling 240 of the external charging circuit 202 with the conductive housing 230.

The external charging circuit 202 may include a signal generator 210, a parallel resonator 250, and a series resonator 214. In a particular embodiment, the signal generator 210 may correspond to the signal generator 128 of FIG. 1 and may operate in a substantially similar manner, the parallel resonator 250 may correspond to the parallel resonator 124 of FIG. 1 and may operate in a substantially similar manner, and the series resonator 214 may correspond to the series resonator 127 of FIG. 1 and may operate in a substantially similar manner. The signal generator 210 may generate a charging signal having high frequency components within the first frequency band (e.g., about 60 kHz to about 100 kHz, and/or about 50 MHz to 100 MHz) and having low frequency components within the second frequency band (e.g., about 9 kHz to about 11 kHz).

The series resonator 214 may include a capacitor 212, a resistor 216 (e.g., may correspond to resistive losses of the primary coil 218), and a primary coil 218 coupled in series. For example, a second terminal of the capacitor 212 may be coupled to a first terminal of the resistor 214, and a second terminal of the resistor 214 may be coupled to a first terminal of the primary coil 218. A second terminal of the signal generator 210 may be coupled to a second terminal of the primary coil 218. The arrangement of the components of the series resonator 214 may change in other embodiments.

The primary coil 218 may correspond to the primary coil 126 of FIG. 1 and may operate in a substantially similar manner. The primary coil 218 may include a radial inductor configured to radiate outward and generate a magnetic field or an electromagnetic field to facilitate inductive coupling 240 (and thus energy transfer) with the secondary coil 220. The series resonator 214 may exhibit capacitance via the capacitor 212, resistance via the resistor 216, and inductance via the primary coil 218. Thus, the series resonator 214 is also an RLC circuit. In a particular embodiment, other circuit elements of the external charging circuit 202 may contribute to the resistance of the series resonator 214. In a particular embodiment, the resonant frequency of the series resonator 214 may be about 10 kHz (e.g., within the second frequency band). The resonant frequency is an efficient frequency at which to operate the series resonator 214 since losses due to impedance and capacitance are reduced. Another characteristic of the resonant frequency of an RLC circuit is that, at the resonant frequency, current and voltage of a signal applied to the RLC circuit are in phase.

The parallel resonator 250 may include a parallel resistor 254 (e.g., may correspond to resistive losses of the parallel inductor 252) coupled in series with a parallel inductor 252. The parallel resonator 250 may also include a parallel capacitor 256 coupled in parallel with the parallel resistor 254 and the parallel inductor 252. The arrangement or order of the components of the parallel resonator 250 may be different in other embodiments. Thus, the parallel resonator 250 is also an RLC circuit. In a particular embodiment, the resonant frequency of the parallel resonator 250 may be within the first frequency band (e.g., about 75 kHz, and/or about 85 MHz). The parallel inductor 252 may be a torodial inductor that is coupled to a board of the external charging circuit 202. For example, the parallel inductor 252 may radiate inward as to reduce or eliminate radiation caused by the parallel resonator 250.

The parallel resonator 250 is configured to reduce noise and radiation generated in the first frequency band at the primary coil 218 of the series resonator 214 that would otherwise be caused by the charging signal. For example, the parallel resonator 250 may substantially inhibit (e.g., filter, block or prevent) harmonics corresponding to the high frequency components (e.g., frequency components within the first frequency band) of the charging signal. In a particular embodiment, the parallel resonator 250 may resonate in response to the high frequency components of the charging signal. For example, the parallel resonator 250 may resonate in response to frequency components within the first frequency band (e.g., frequency components ranging from about 60 kHz to about 100 kHz, and/or 50 MHz to 100 MHz). When the parallel resonator 250 resonates, the parallel resonator 250 may operate in a manner similar to an open circuit and substantially inhibit or filter the high frequency components from being provided to the series resonator 214. Inhibiting (e.g., filtering) the high frequency components of the charging signal from being provided to the series resonator 214 may reduce radiation of signals in the first frequency band at the primary coil 218.

The parallel resonator 250 may be designed to filter particular harmonics of the charging signal. For example, the parallel resonator 250 may resonate, and thus filter particular frequency components of the charging signal, based on the capacitance of the parallel capacitor 256 and the inductance of the parallel inductor 252. In a particular embodiment, multiple parallel resonators may be used in series to notch out multiple frequency components of concern. For example, a second parallel resonator (not shown) with a capacitance and inductance designed to filter out frequency components within a third frequency band (e.g., from about 20 kHz to 50 kHz, or 50 MHz to 100 MHz) may be added to the external charging circuit 202.

The parallel resonator 250 is also configured to contribute to the inductance of the series resonator 214. For example, the parallel resonator 250 may function in a manner similar to an inductor in response to the low frequency components of the charging signal and may provide the low frequency components of the charging signal to the series resonator 214. The inductance of the parallel resonator 250 may contribute to the effective inductance of the series resonator 214. The parallel inductor 252 may be a torodial inductor coupled to a circuit board of the external charging circuit 202 to reduce or eliminate radiation at the parallel resonator 250. Thus, a smaller primary coil 218 may be used in the series resonator 214 without reducing an effective inductance of the external charging circuit 202.

During operation, the signal generator 210 may generate a charging signal having high frequency components and low frequency components and may provide the charging signal to the parallel resonator 250. The parallel resonator 250 may filter the high frequency components of the charging signal from propagating to the series resonator 214. The parallel resonator 250 may provide the low frequency components of the charging signal to the series resonator 214. For example, in response to the high frequency components of the charging signal, the parallel resonator 250 may function as an open circuit and substantially inhibit (e.g., filter, block, or prevent) portions of the charging signal that correspond to the high frequency components from propagating to the series resonator 214. In response to the low frequency components of the charging signal, the parallel resonator 250 may function as an inductor and provide the low frequency components of the charging signal to the series resonator 202. The low frequency components of the charging signal provided to the series resonator 214 may cause the series resonator 214 to resonate, enabling the primary coil 218 to inductively couple 240 to the secondary coil 220 of the implantable medical device 102 to provide a current to the secondary coil 220.

A voltage based on the current at the secondary coil 220 is provided to the rechargeable power supply 224 to recharge the implantable medical device 204. Radiation and noise in a high frequency range may be reduced at the primary coil 126 during inductive coupling 240 in response to parallel resonator 240 filtering the high frequency components of the charging signal from the series resonator 214 and providing the low frequency components of the charging signal to the series resonator 214.

The parallel resonator 250 may also facilitate simultaneous data communication with the implantable medical device 204 using a first frequency (e.g., 75 kHz) and recharging of the implantable medical device 204 using a second frequency (e.g., 10 kHz). For example, charging the implantable medical device 204 using the second frequency within the second frequency band while the parallel resonator 250 filters the first frequency within the first frequency band may reduce a likelihood of signal interference, which may cause communication errors.

Figure 3:
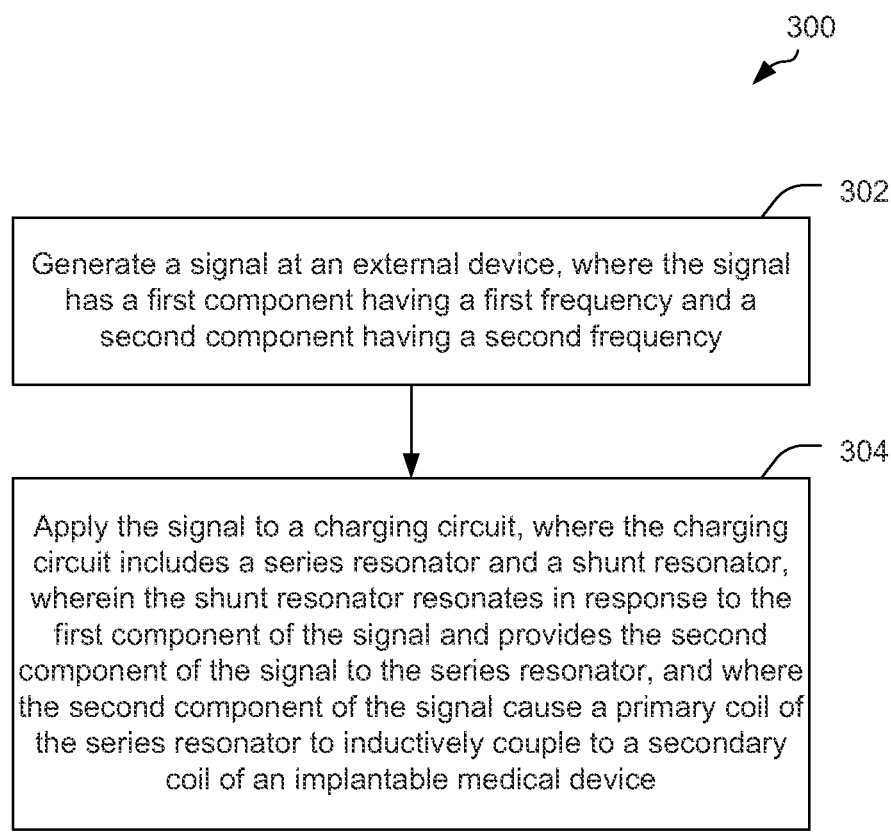
FIG. 3 is flow chart of a particular embodiment of a method of charging an implantable medical device.

FIG. 3 is a flow chart of a particular method 300 of charging an implantable medical device. For example, the method 300 may be performed by an external charging system and the components thereof, such as the charging circuit 122 of FIG. 1, the parallel resonator 124 of FIG. 1, the signal generator 128 of FIG. 1, the series resonator 127 of FIG. 1, the external charging system 202 of FIG. 2, the signal generator 210 of FIG. 2, the parallel resonator 250 of FIG. 2, the series resonator 214 of FIG. 2, or any combination thereof. The method 300 may be performed during charging of an implantable medical device, such as the implantable medical device 102 of FIG. 1 or the implantable medical device 204 of FIG. 2. In a particular embodiment, the implantable medical device may include a nerve stimulation device. The nerve stimulation device may include a secondary coil, a battery and a battery charging circuit within a conductive housing. The secondary coil may be responsive to a charging signal applied to the primary coil of an external charging circuit to provide energy to charge the battery. In this particular embodiment, the battery may be charged during data communication with the implantable medical device.

The method 300 may include generating a signal at an external device, at 302. For example, in FIG. 1, the signal generator 128 may generate the charging signal. The charging signal may have a first component (e.g., a high frequency component) having a first frequency within the first frequency band (e.g., about 60 kHz to about 100 kHz, and/or 50 MHz to 100 MHz) caused by the charging signal harmonics and/or switching noise from the signal generator. The charging signal may also have a second component (e.g., a low frequency component) having a second frequency within the second frequency band (e.g., about 9 kHz to 11 kHz). As another example, in FIG. 2, the signal generator 210 may generate the charging signal.

The signal may be applied to a charging circuit, at 304. For example, in FIG. 1, the signal generator 128 may apply the charging signal to the parallel resonator 124 of the charging circuit 122. The parallel resonator 124 may resonate in response to the first component of the charging signal. The parallel resonator 124 may function as an open circuit and substantially inhibit (e.g., filter, block, or prevent) the first component of the charging signal from propagating to the series resonator 127. The parallel resonator 124 may provide the second component of the charging signal to the series resonator 127. The second component of the charging signal may cause the primary coil 126 of the series resonator 127 to inductively couple 152 to the secondary coil 130 of the implantable medical device 102.

As another example, in FIG. 2, the signal generator 210 may apply the charging signal to the parallel resonator 250 of the external charging circuit 202. The parallel resonator 250 may resonate in response to the first component of the charging signal. The parallel resonator 250 may function as an open circuit and substantially inhibit (e.g., filter, block, or prevent) the first component of the charging signal from propagating to the series resonator 214. In response to the second component of the charging signal, the parallel resonator 250 may function as an inductor and provide the second component of the charging signal to the series resonator 214. The second component of the charging signal may cause the primary coil 218 of the series resonator 214 to inductively couple 240 to the secondary coil 220 of the implantable medical device 204.

In a particular embodiment, the series resonator may resonate in response to the second component of the signal. For example, in FIG. 1, the series resonator 127 may resonate in response to the low frequency component of the charging signal. As another example, in FIG. 2, the series resonator 214 may resonate in response to the low frequency component of the charging signal.

In a particular embodiment, energy may be inductively transferred to the secondary coil within the implantable medical device via the primary coil of the charging circuit to recharge the implantable medical device. For example, in FIG. 1, the primary coil 126 of the series resonator 127 may inductively couple 152 to the secondary coil 130 of the implantable medical device 102 in response to the second component of the charging signal. A current may be generated at the secondary coil 130 based on the inductive coupling 152, and the battery charging system 114 may apply a charging voltage to the battery 112 in response to the current. As another example, in FIG. 2, the primary coil 218 may inductively couple 240 to the secondary coil 220 of the implantable medical device 204 in response to the second component of the charging signal. The secondary coil 220 may generate a current based on the inductive coupling 152, and a charging voltage may be applied to the rectifier 223 and then to the rechargeable power supply 224 in response to the current.

The method 300 may enable an external device to simultaneously communicate data to and from an implantable medical device at a first frequency (e.g., a high frequency) and to charge the implantable medical device at a second frequency (e.g., a low frequency). For example, the parallel resonator 124 may substantially inhibit (e.g., filter, block, or prevent) high frequency components of the charging signal from the series resonator 127. Filtering the high frequency components may reduce radiation and noise at a frequency of the high frequency components during inductive coupling 152, and may also permit inductive recharging using the second frequency corresponding to the low frequency components of the charging signal (as opposed to inductive recharging using both the high frequency components and the low frequency components of the charging signal). Communicating data over a first frequency and charging over a second frequency may reduce interference and errors during data communication.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. For example, method steps may be performed in a different order than is shown in the figures or one or more method steps may be omitted. Accordingly, the disclosure and the figures are to be regarded as illustrative rather than restrictive.

Moreover, although specific embodiments have been illustrated and described herein, it should be appreciated that any subsequent arrangement designed to achieve the same or similar results may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, the claimed subject matter may be directed to less than all of the features of any of the disclosed embodiments.

What is claimed is:

1. An implantable medical device charging apparatus comprising:
a charging circuit, wherein the charging circuit includes:
a series resonator responsive to a signal applied to the charging circuit, the series resonator configured to inductively couple to a secondary coil within an implantable medical device to transfer energy to the secondary coil, the signal having a first component having a first frequency within a first frequency band and a second component having a second frequency within a second frequency band; and
a first parallel resonator coupled to the series resonator, the first parallel resonator configured to filter the first component of the signal from propagating to the series resonator.

2. The implantable medical device charging apparatus of claim 1, wherein the series resonator includes a primary coil and the first parallel resonator includes a parallel inductor.

3. The implantable medical device charging apparatus of claim 2, wherein the primary coil is a radial inductor and wherein the parallel inductor is a torodial inductor.

4. The implantable medical device charging apparatus of claim 1, wherein the charging circuit further comprises:
a signal generator configured to generate the signal, wherein the first component is switching noise caused by the signal generator.

5. The implantable medical device charging apparatus of claim 4, wherein the first frequency band ranges from 50 megahertz (MHz) to 100 MHz.

6. The implantable medical device charging apparatus of claim 1, wherein the first parallel resonator is configured to provide the second component of the signal to the series resonator, wherein the second frequency band has a lower frequency range than the first frequency band, wherein the series resonator resonates in response to receiving the second component of the signal.

7. The implantable medical device charging apparatus of claim 1, wherein the charging circuit further comprises:
a signal generator configured to generate the signal, wherein the first component is a harmonic of the signal.

8. The implantable medical device charging apparatus of claim 7, wherein the first frequency band ranges from 60 kilohertz (kHz) to 100 kHz.

9. The implantable medical device charging apparatus of claim 1, wherein the second frequency band ranges from 9 kilohertz (kHz) to 11 kHz.

10. The implantable medical device charging apparatus of claim 1, wherein the charging circuit further comprises:
a second parallel resonator coupled in series with the first parallel resonator and the series resonator, the second parallel resonator configured to filter a third component having a third frequency within a third frequency band of the signal from propagating to the series resonator.

11. The implantable medical device charging apparatus of claim 10, wherein the first frequency band ranges from 60 kilohertz (kHz) to 100 kHz and the third frequency band ranges from 50 megahertz (MHz) to 100 MHz.

12. A method comprising:
generating a signal at an implantable medical device charging apparatus, wherein the signal has a first component having a first frequency within a first frequency band and has a second component having a second frequency within a second frequency band;
applying the signal to a charging circuit, wherein the charging circuit includes a series resonator and a first parallel resonator, wherein the first parallel resonator inhibits the first component of the signal from propagating to the series resonator and provides the second component of the signal to the series resonator, and wherein the second component of the signal causes a primary coil of the series resonator to inductively couple to a secondary coil of an implantable medical device.

13. The method of claim 12, wherein the series resonator resonates in response to the second component of the signal.

14. The method of claim 12, wherein the first parallel resonator resonates in response to the first component of the signal to inhibit the first component of the signal from propagating to the series resonator.

15. The method of claim 12, wherein the first frequency band ranges from 60 kilohertz (kHz) to 100 kHz or from 50 megahertz (MHz) to 100 MHz, and wherein the second frequency band ranges from 9 kHz to 11 kHz.

16. The method of claim 12, further comprising communicating data to a receiver within the implantable medical device, wherein the data is communicated over the first frequency band and wherein the implantable medical device charging apparatus charges the implantable medical device over the second frequency band.

17. The method of claim 12, wherein the signal has a third component having a third frequency within a third frequency band, wherein the charging circuit includes a second parallel resonator, wherein the second parallel resonator inhibits the third component of the signal from propagating to the series resonator and provides the second component of the signal to the series resonator.

18. The method of claim 17, wherein the first frequency band ranges from 60 kilohertz (kHz) to 100 kHz and the third frequency band ranges from 50 megahertz (MHz) to 100 MHz.

19. A circuit comprising:
a signal generator configured to generate a signal, the signal having a first component having a first frequency within a first frequency band and a second component having a second frequency within a second frequency band;
a parallel resonator coupled to the signal generator, wherein the parallel resonator includes a parallel inductor and a parallel capacitor;
a series resonator coupled to the parallel resonator, the series resonator configured to inductively transfer energy to a secondary coil within an implantable medical device, wherein the series resonator includes a capacitor and a primary coil, wherein the parallel resonator is configured to inhibit the first component from propagating to the series resonator and to provide the second component of the signal to the series resonator.

20. The circuit of claim 19, wherein the first component is a harmonic of the signal or switching noise caused by the signal generator.

* * * * *